United States Patent
Davenport et al.

(10) Patent No.: US 9,763,806 B2
(45) Date of Patent: Sep. 19, 2017

(54) METHOD AND APPARATUS FOR IMPLANTING A PROSTHESIS

(71) Applicant: Biomet Manufacturing, LLC, Warsaw, IN (US)

(72) Inventors: Austen Davenport, Columbia City, IN (US); Tyler D. Witt, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 691 days.

(21) Appl. No.: 13/658,620

(22) Filed: Oct. 23, 2012

(65) Prior Publication Data
US 2014/0114321 A1  Apr. 24, 2014

(51) Int. Cl.
- A61B 17/58 (2006.01)
- A61B 17/60 (2006.01)
- A61F 2/00 (2006.01)
- A61F 2/46 (2006.01)
- A61F 2/30 (2006.01)

(52) U.S. Cl.
CPC .. A61F 2/4609 (2013.01); A61F 2002/30138 (2013.01); A61F 2002/30479 (2013.01); A61F 2002/30505 (2013.01); A61F 2002/4627 (2013.01); A61F 2002/4629 (2013.01); A61F 2002/4681 (2013.01)

(58) Field of Classification Search
CPC .................................................. A61F 2/4609
USPC ......................................................... 606/91
See application file for complete search history.

(56) References Cited

U.S. PATENT DOCUMENTS

| | | |
|---|---|---|
| 4,023,572 A | 5/1977 | Weigand et al. |
| 4,716,894 A | 1/1988 | Lazzeri et al. |
| 5,236,433 A | 8/1993 | Salyer |
| 5,683,399 A | 11/1997 | Jones |
| 5,954,727 A | 9/1999 | Collazo |
| 6,626,913 B1 | 9/2003 | McKinnon et al. |
| 7,296,804 B2 | 11/2007 | Lechot et al. |
| 7,396,357 B2 | 7/2008 | Tornier et al. |
| 7,621,921 B2* | 11/2009 | Parker ....................... A61F 2/34 606/91 |
| 7,682,363 B2 | 3/2010 | Burgi et al. |
| 7,998,147 B2 | 8/2011 | Santarella et al. |
| 2004/0153074 A1* | 8/2004 | Bojarski ............ A61B 17/0401 606/232 |
| 2005/0038443 A1 | 2/2005 | Hedley et al. |
| 2009/0069823 A1* | 3/2009 | Foerster et al. ............... 606/139 |

(Continued)

FOREIGN PATENT DOCUMENTS

| | | |
|---|---|---|
| EP | 1813229 A1 | 8/2007 |
| EP | 2345392 A1 | 7/2011 |

*Primary Examiner* — David Isabella
*Assistant Examiner* — Christine Nelson
(74) *Attorney, Agent, or Firm* — Schwegman Lundberg & Woessner, P.A.

(57) ABSTRACT

Disclosed is a system for engaging and holding a prosthesis both axially and rotationally relative to an inserter assembly. The inserter assembly can engage an acetabular prosthesis in a selected position, such as axially, with a first portion and then or subsequently engage the acetabular prosthesis with a second portion in a rotationally fixed manner. The acetabular prosthesis can then be inserted into a prepared acetabulum according to a disclosed method with the inserter assembly. The inserter assembly can then be removed from the acetabular prosthesis to allow for reduction of a femur.

14 Claims, 5 Drawing Sheets

(56) References Cited

U.S. PATENT DOCUMENTS

| | | |
|---|---|---|
| 2009/0112219 A1 | 4/2009 | Daniels et al. |
| 2009/0112220 A1 | 4/2009 | Kraus |
| 2010/0049257 A1 | 2/2010 | Parker |
| 2011/0218582 A1* | 9/2011 | Smith et al. ............... 606/86 R |

* cited by examiner

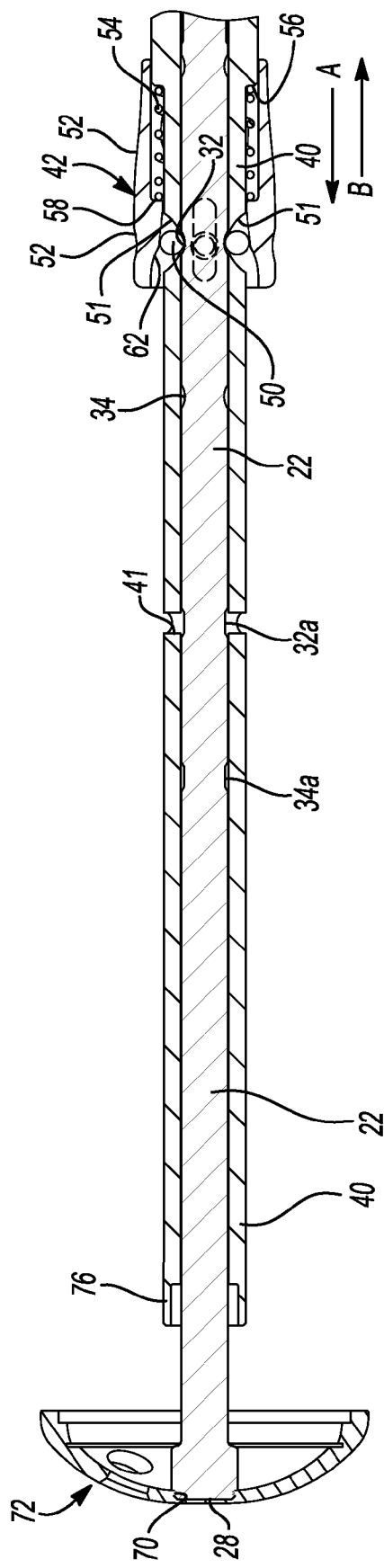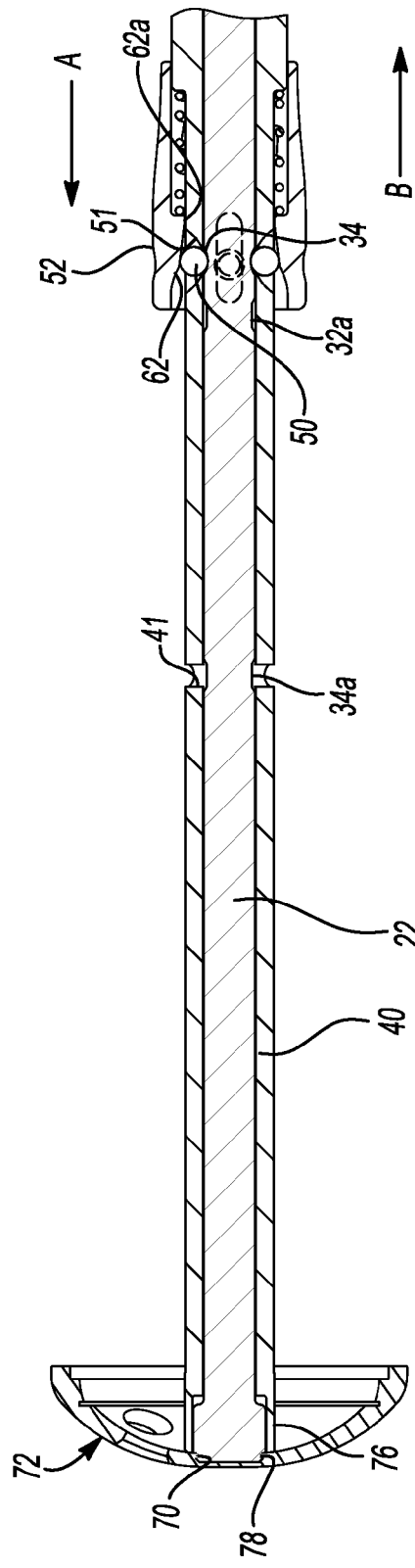

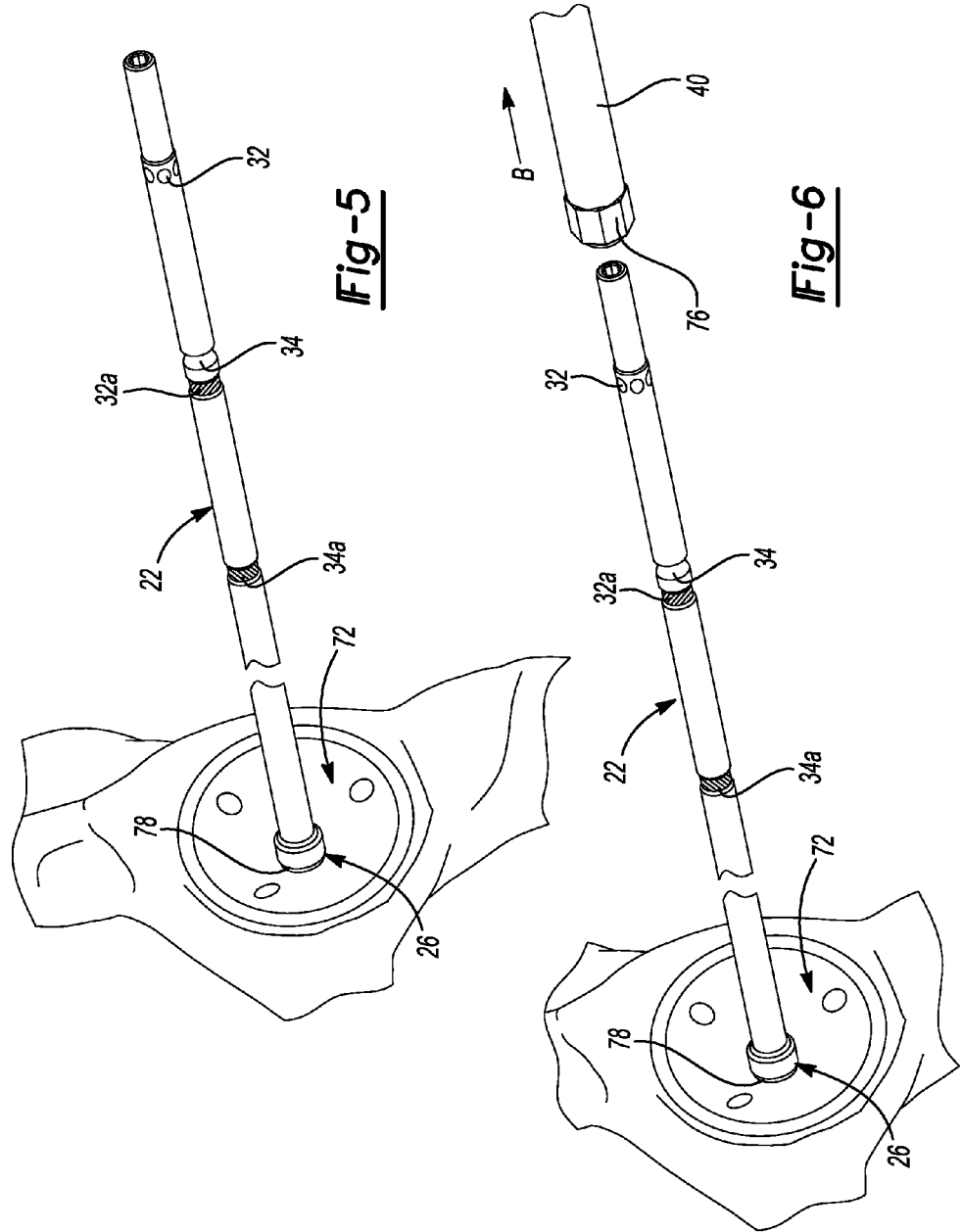

METHOD AND APPARATUS FOR IMPLANTING A PROSTHESIS

FIELD

The subject disclosure relates to instrumentation, and particularly to surgical implantation instrumentation for positioning an acetabular cup.

BACKGROUND

This section provides background information related to the present disclosure which is not necessarily prior art. In performing a procedure on a patient, a prosthesis can be used to replace or augment a natural anatomical feature. For example, due to age, injury, disease, or other causes, a portion of the anatomy may need to be replaced or resurfaced. Examples include replacing an acetabulum on a patient either in conjunction with or separate from replacing or resurfacing a femoral head. An acetabular prosthesis is generally positioned within a prepared acetabulum.

Positioning an acetabular prosthesis within a prepared acetabulum can include various dexterous movements. The acetabular prosthesis is generally positioned within the acetabulum in a selected alignment and position. The alignment of the acetabular prosthesis is generally selected to be relative to the natural anatomy. The prosthesis includes a central axis that is generally aligned and positioned or is selected to be aligned and positioned with a portion of the natural anatomy. In positioning the acetabular prosthesis in the selected position, both position and axial alignment can be selected.

When positioning the acetabular prosthesis, it also needs to be engaged into the acetabulum with a selected force to ensure proper seating and positioning of the acetabular prosthesis. Accordingly, positioning the acetabular prosthesis generally requires dexterity on the part of the user, such as a surgeon, to position the acetabular prosthesis appropriately in a patient's anatomy. Then a force is applied to assist in fixing the prosthesis in the pelvis.

SUMMARY

This section provides a general summary of the disclosure, and is not a comprehensive disclosure of its full scope or all of its features.

An instrument to position an acetabular prosthesis in a prepared acetabulum is disclosed. The instrument can engage the acetabular prosthesis to establish both position and rotation control of the acetabular prosthesis. The acetabular engagement instrument can include at least a first portion to thread into an acetabular prosthesis and a second portion to engage a rotational control or holding portion of the acetabular prosthesis. Generally, the threaded portion can be positioned within an exterior member that can engage the acetabular prosthesis to fix rotation of the acetabular prosthesis relative to both of the threaded member and the exterior member.

A process of positioning an acetabular prosthesis in a prepared acetabulum can include engaging the acetabular prosthesis for positioning relative to the prepared acetabulum. Engaging the acetabular prosthesis with an insertion instrument to fix it in both a position and rotation relative to the instrument can assist in positioning the acetabular prosthesis in the anatomy in a selected position and orientation. The acetabular prosthesis can be positioned in the prepared acetabulum both at a selected position and in a selected orientation between a central axis of the acetabular prosthesis and the anatomy.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 2 is a detailed cross-sectional view of the acetabular inserter of FIG. 1 connected to an acetabular prosthesis with a portion of the inserter assembly in a first configuration;

FIG. 3 is a detailed cross-sectional view of the inserter of FIG. 1 with a portion thereof in a second configuration;

FIG. 5 is a perspective view of a threaded rod portion of the inserter connected to an acetabular prosthesis;

FIG. 6 is a detailed exploded view of a portion of the acetabular inserter interconnected with an acetabular prosthesis;

Corresponding reference numerals indicate corresponding parts throughout the several views of the drawings.

DETAILED DESCRIPTION

Example embodiments will now be described more fully with reference to the accompanying drawings.

Figure 1:
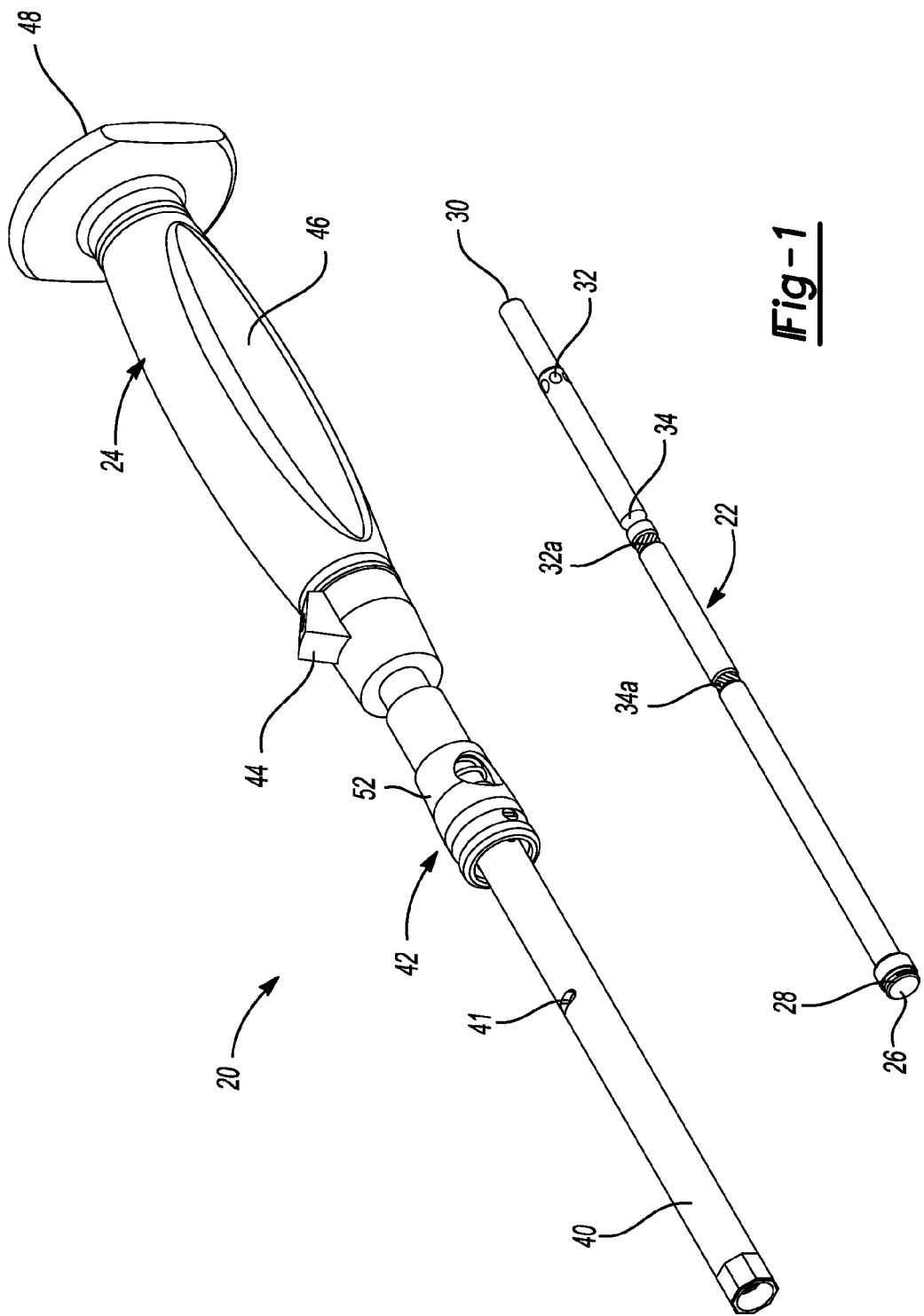
FIG. 1 is an exploded view of an acetabular inserter assembly.
Figure 4:
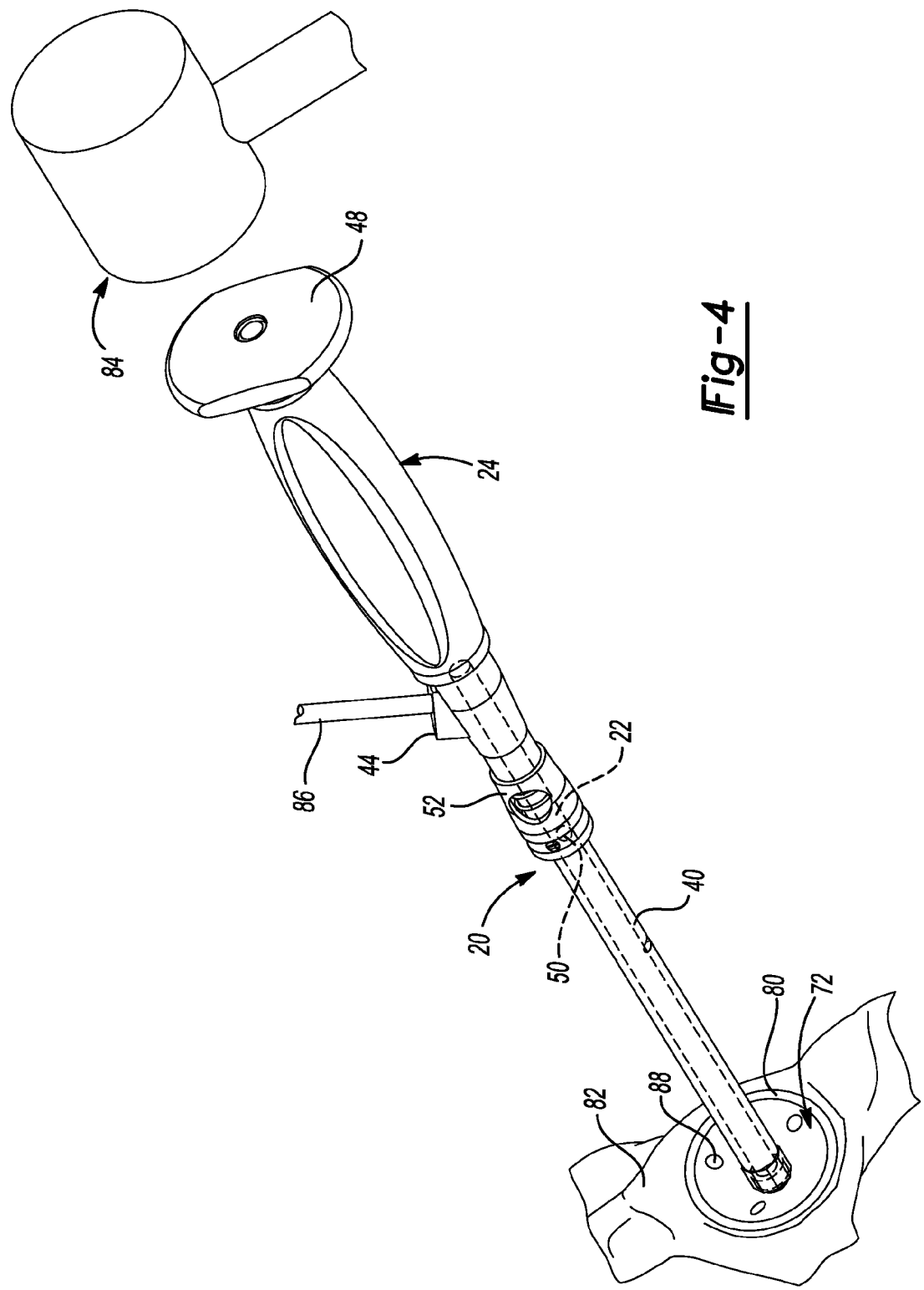
FIG. 4 is a perspective environmental view of the inserter positioning an acetabular prosthesis.

An acetabular prosthesis positioning instrument assembly (also referred to as an acetabular inserter) 20 is illustrated in FIGS. 1 and 2. Generally, the acetabular inserter 20 can include a first threaded rod member 22 and second handle body member 24. The threaded rod member 22 can include a threaded first end 26 that can include or have formed on the exterior surface thereof a thread 28. The thread 28, as discussed herein, can engage an interior thread of an acetabular prosthesis 72 (see FIG. 2) to secure or hold the acetabular prosthesis in a selected position relative to the threaded rod 22 and, as discussed further herein, the handle body 24 for holding the acetabular prosthesis 72 relative to the acetabular inserter 20.

Generally, the threaded rod 22 can extend from the first end 26 to a second end 30. Formed into an exterior surface of the threaded rod 22, between the first end 26 and the second end 30, can be a first detent or a set of detents 32 and a second detent or set of detents 34. As discussed herein, the first and second set of detents 32, 34 can be engaged by an engagement or handle holding mechanism of the handle body 24 to hold the threaded rod 22 at a selected position relative to the handle body 24. Also, the detents 32, 34 can include any depression formed in the surface of the rod 22, such as a continuous groove or discontinuous depressions. As illustrated in FIG. 1, the first detent 32 can be formed as one or more separate and distinct depressions in the threaded rod 22. The second detent 34 can be formed as a single continuous groove in the threaded rod 22. It is understood, however, that either or both of the first and second detents 32, 34 can be formed as a continuous groove or distinct depressions. The threaded rod 22 can be threaded into the acetabular prosthesis 72, as further discussed herein. The threaded rod 22 can then be positioned into a handle extension 40 of the handle body 24. The handle extension 40 can be formed as a sleeve or cannulated tube that extends from the handle body 24 into which or through which the threaded rod 22 can be passed. The handle extension 40 of the handle body 24 can include a mark window 41 and a locking or rod engagement mechanism 42, as further discussed herein. The handle body 24 can further include an attachment site for an alignment rod connection mechanism or position 44. As is generally understood in the art, an alignment rod can be used for aligning the prosthesis 72 that is connected to the handle body 24. Additionally, the handle body 24 can include a grasping or gripping portion 46 that can include various non-slip and cushioning portions such as knurling, a hard rubber, or rubber handle. Furthermore, the handle body 24 can include a strike plate or impaction plate 48 to allow for impacting the prosthesis 72 into a patient once the prosthesis is interconnected with the handle body 24, as discussed further herein. Additionally, as discussed further herein, it is understood that the threaded rod 22 can be connected to the handle body 24 prior to being threaded into or onto the acetabular prosthesis 72. Accordingly, the acetabular prosthesis 72 can be interconnected with the threaded rod 22 either prior to the threaded rod being engaged in the handle body 24, or after the threaded rod 22 is engaged in the handle body 24.

According to various embodiments, the threaded rod 22 can be engaged in the handle extension 40, as illustrated in FIG. 2. A fixing or locking member can include a ball bearing 50 that can engage the first set of detents 32 or the second set of detents 34. The locking member 50 can also be at least partially housed in a passage 51 of the handle extension 40. It is understood that one or a plurality of the ball bearings 50 can be provided to engage one or all of the detents 32, 34. The locking mechanism 42 can include the ball bearing 50 and can further include a locking sleeve or locking tube 52. The locking sleeve 52 can include a biasing spring 54 that engages between a wall 56 of the handle portion 46 and a lower surface or engaging surface 58 of the locking sleeve 52 of the locking mechanism 42. The locking sleeve 52 can further include a ramp surface 62 to engage the ball bearings 50 into the detents 32, 34. When the rod 22 is in the first position, the spring 54 can bias the locking sleeve 52 towards the ball bearing 50 to engage the ball bearing 50 into the first detent 32. Accordingly, the spring 54 can bias the sleeve 52 generally in the direction of Arrow A.

To allow the threaded rod 22 to move past the ball bearings 50 to allow the first detents 32 to be positioned relative to the bearings 50, the sleeve 52 can be moved generally in the direction of Arrow B by force of a user, such as a surgeon or a surgical technician. Accordingly, the sleeve 52 can be moved in the direction of Arrow B to allow the ramp surface 62 to disengage the ball bearings 50. The threaded rod 22 can then be positioned into the handle extension 40 and the rod 22 can bias or move the ball bearings 50 out an interior of the handle extension 40. The locking sleeve 52 can then be disengaged and the biasing spring 54 can move generally in the direction of Arrow A to allow the ramp surface 62 to engage the ball bearings 50. When the first set of detents 32 is aligned with the ball bearings 50, the ball bearings can move into the first detents 32 and the locking sleeve 52 can, once the locking bearings are in the first detents 32, move to a final position to urge or force the ball bearings 50 into the detents 32. Also, when the locking bearing 50 is engaged in the first detent 32 a first demarcation 32a on the rod 20 can be viewed through the mark window 41 of the handle extension 40, as illustrated in FIG. 2.

As illustrated in FIG. 1, the first detent 32 can be provided or formed as a plurality of distinct and separate depressions in the threaded rod 22. As the locking bearing 50 can also be a separate or distinct bearing member, such as a ball bearing member, the ball bearing as a separate member can engage a single distinct depression in the threaded rod 22. As the locking ball bearing 50 is urged through the passage 51 of the handle extension 40 due to the locking sleeve 52, the ball bearing 50 is pushed or moved into the first detent 32. The ball bearing 50, however, is maintained at least partially within the wall of the handle extension 40 such that the locking sleeve 52 urges the ball bearing 50 into the first detent 32 and into the passage 51 such that the ball bearing can engage and interconnect the threaded rod 22 and the handle extension 40. Since the ball bearing 50 is engaged into a distinct portion, such as one detent 32, and in the passage 51 of the handle extension 40, the handle extension 40 can be rotationally fixed relative to the threaded rod 22.

As illustrated in FIG. 2, the threaded rod 22, is engaged with the ball bearing 50 and the first detent 32, at least when the threads 28 of the threaded rod are displaced a distance from and end of the handle extension 40. Accordingly, the threaded rod 22 and the handle 24 can be rotated relative to the acetabular cup 72 without having the acetabular cup engage a portion of the handle extension 40. This allows the threaded rod 22 to be threaded into the acetabular prosthesis prior to the prosthesis being moved to engage the handle extension 40. Thus, a separate or additional threading mechanism is not necessary to thread the threaded rod 22 onto the prosthesis. Thus, once the ball bearing 50 is urged into the detents 32, the tool handle 24 and rod 22 assembly can be rotated to thread the threads 28 of the threaded end 26 into a selected threaded hole 70 of the acetabular prosthesis 72.

As is generally understood, the acetabular prosthesis 72 can be positioned within a prepared acetabulum of a patient, as discussed further herein. The threaded rod 22 can be threaded into the threaded hole 70 of the acetabular prosthesis 72 to fix the acetabular prosthesis 72 in at least one degree of freedom, initially axially, relative to the threaded rod 22. The threaded rod 22, however, can unthread during positioning of the acetabular prosthesis 72 if it is only threaded into the threaded hole 70 of the acetabular prosthesis 72. Fixation of the prosthesis 72 to the rod 22 can include rotational fixation relative to the rod 22. Accordingly, providing a rotational fixation between the acetabular prosthesis 72 and the acetabular inserter 20 can be selected. Also, rotational fixation assists in aligning the prosthesis 72 during implantation.

Once the acetabular prosthesis is engaged with the threaded rod 22 the handle extension 40 can be moved towards the acetabular prosthesis 72, as illustrated in FIG. 3, generally in the direction of Arrow A, as discussed below. When the handle extension 40 engages the prosthesis 72 a rotational or keyed locking portion 76 of the handle extension 40 can engage a similarly or complementary shaped rotation control portion 78 of the acetabular prosthesis 72.

The rotational control portion 76 of the inserter 20 and the acetabular prosthesis rotational control 78 can be complementary shaped or keyed in any appropriate shape or configuration. For example, a circle with a flat side can be used to engage and lock the inserter 20 relative to the acetabular prosthesis 72. Also, other selected shapes such as square shapes, flat sided polygons, and other appropriate shapes can be provided to allow for an engagement between the inserter 20 and the acetabular prosthesis 72. Generally, the inserter rotation control portion 76 and the acetabular prosthesis rotational control figuration 78 are complementary such that the inserter 20, including the handle extension 40, can be positioned to engage the acetabular prosthesis 72 to rotationally fix the acetabular prosthesis 72 relative to the inserter 20. In this way, rotation of the handle 46 will translate directly to rotation of the prosthesis 72 giving a user version control of the prosthesis 72 during implantation.

Figures 7, 8:
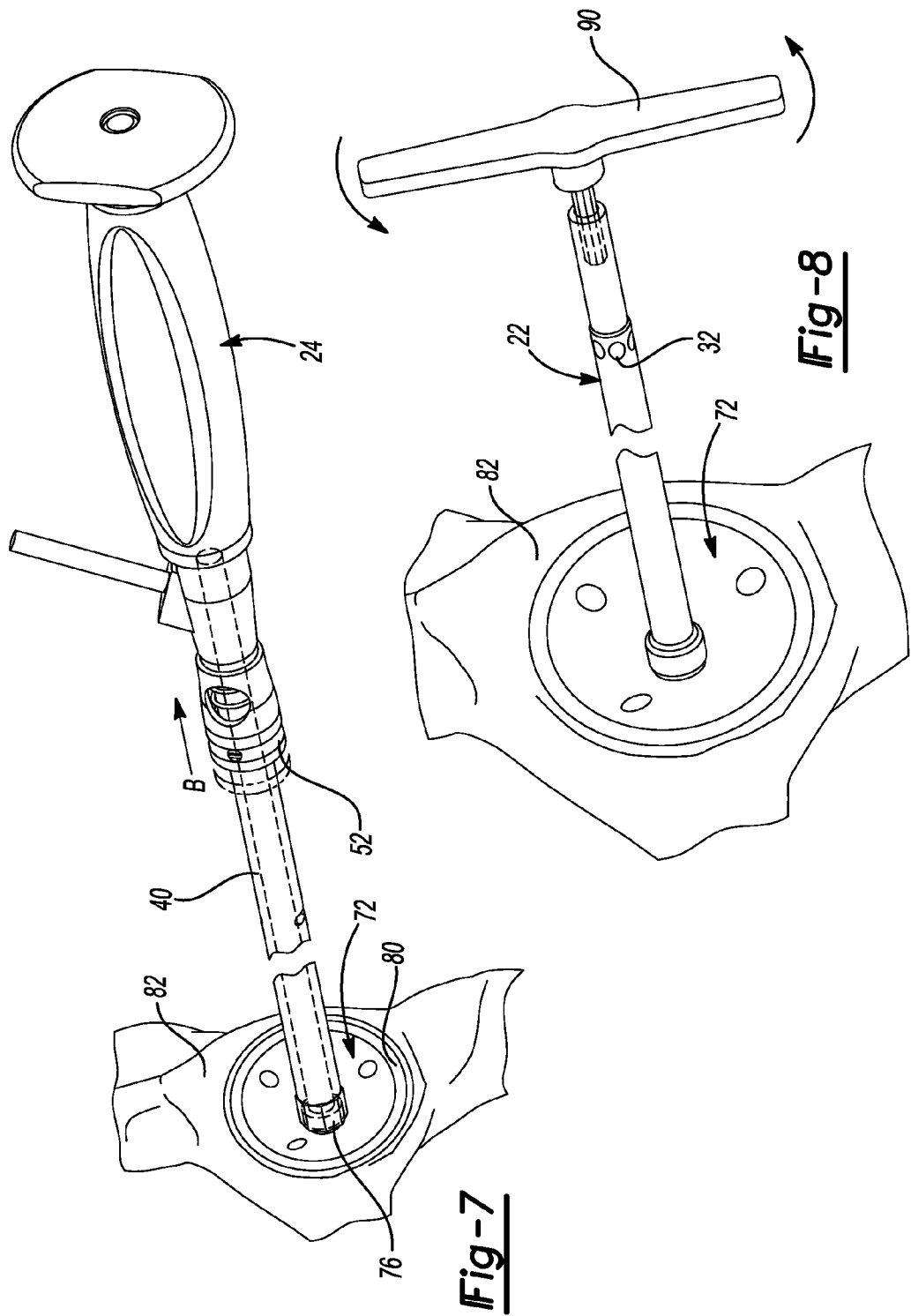
FIG. 7 is an environmental view of an acetabular prosthesis inserter being removed from a portion of the inserter assembly after positioning the acetabular prosthesis.
FIG. 8 is a perspective environmental view of removing a portion of the acetabular prosthesis inserter assembly after removing a first portion of the inserter assembly.

As illustrated in FIG. 3, to move and engage the handle extension 40, and particularly the rotation control portion 76 of handle extension 40 with the acetabular rotation control portion 78 of the acetabular prosthesis 72, the threaded rod 22 can be moved generally in the direction of Arrow B towards the handle 46 to allow, move, or urge the acetabular prosthesis 72 into engagement with the handle extension 40. As discussed above, the threaded rod 22 can be threaded into the threaded opening 70 of the acetabular prosthesis 72 by rotating either or both of the acetabular prosthesis 72 and/or the rod 22 in an appropriate rotational direction. The engagement of the rotation control portion 76 of handle extension 40 with the acetabular rotation control portion 78 of the acetabular prosthesis 72 can rotationally fix the prosthesis 72 relative to the handle extension 40. This rotational fixation can allow a user to control version (i.e. rotation control) of the prosthesis during implantation, as illustrated in FIG. 7.

Once the threaded rod 22 is engaged to the acetabular prosthesis 72, in an appropriate manner, such as to a selected torque, the threaded rod 22 that has engaged the acetabular prosthesis 72 can be moved in the direction of Arrow B. The locking sleeve 52 which has previously engaged to the ball bearings 50, can be moved in the direction of Arrow B to allow the ramp surface 62 to disengage the bearings 50. Once the locking sleeve 52 has moved to allow the ramp surface 62 to disengage or not contact the bearings 50, in an unlocked position, generally near locking portion upper region 62a of the ramp surface 62, the bearings 50 can be forced out of the first set of detents 32 and the rod 22 can move within the handle extension 40. Accordingly, once the locking sleeve 52 has been moved in the direction of Arrow B, and the bearings have been moved out of the locking portion 62a of the ramp surface 62, the rod 22 can be moved generally in the direction of Arrow B. Once the bearing 50 is out of the detent 32 the locking sleeve 52 can be released to allow the biasing spring 54 to urge the sleeve 52 towards the rotation control portion 76 of handle extension 40 of the handle extension 40. In this manner, once the second set of detents 34 are then moved into general alignment with the ball bearings 50, the ball bearings 50 can move into the detents 34 and the sleeve 52 can be released to be biased to allow the locking portion of the ramp 62a to engage the ball bearings 50 to lock the ball bearings 50 into the second set of the detents 34. Once the ball bearings 50 are locked into the second set of detents 34, the handle extension 40 is generally engaged into the acetabular prosthesis 72. When the handle extension 40 is engaged into the prosthesis 72 the complementary rotational control portions 76, 78 of the handle extension 40 and acetabular prosthesis 72, respectively, are engaged to fix the acetabular prosthesis 72 rotationally relative to the handle extension 40. When the second set of detents 34 are engaged with the locking bearings 50 a second demarcation 34a can be viewed through the mark window 41 in the sleeve.

Once the acetabular prosthesis 72 is engaged onto the inserter 20 by having the complementary interconnection of the anti-rotation control portions 76, 78, the inserter 20 can be used to insert the acetabular prosthesis 72 into a prepared acetabulum 80 of a pelvis 82 of a selected patient. The prepared acetabulum 80 can be prepared in any appropriate manner, such as reaming the acetabulum 80 to prepare it for insertion of the acetabular prosthesis 72. The acetabular prosthesis 72 can be any appropriate acetabular prosthesis such as the _BIOMET RINGLOC®_+ ACETABULAR PROSTHESIS, sold by Biomet, Inc. having a place of business in Warsaw, Ind.

To implant the acetabular prosthesis 72, a mallet or impaction instrument 84 can impact the impaction strike plate 48 of the inserter 20 to impact the acetabular prosthesis 72 into the prepared acetabulum 80. An alignment rod 86 can be engaged in the alignment portion 44 of the handle 24 to assist in the alignment of the acetabular prosthesis 72 relative to the pelvis 82 of the patient. The acetabular prosthesis 72 is generally locked in both position and rotational configuration relative to the inserter assembly 20 by engagement of the threaded rod 22 and the complementary anti-rotation portions 76, 78. Accordingly, the acetabular prosthesis 72 can be positioned within the prepared acetabulum to have a selected position and version, or position of rotation, relative to the pelvis 82 of the patient.

Once the acetabular prosthesis 72 is positioned within the prepared acetabulum 80, the acetabular prosthesis can be otherwise fixed relative to the pelvis 82. Examples include fixation with a screw through a selected fixation hole 88 of the acetabular prosthesis 72 or cement. It is understood, however, that the acetabular prosthesis 72 can be fixed relative to the pelvis 82 in any other selected manner.

The acetabular prosthesis 72 can be positioned relative to the handle 24 according to the various embodiments, such as rotationally or threadingly affixing the threaded rod 22 relative to the acetabular prosthesis 72 prior to inserting the threaded rod 22 into the handle extension 40. For example, as illustrated in FIG. 5, the threaded rod 22 can be threadingly engaged into the acetabular prosthesis 72 prior to the threaded rod 22 being engaged into the handle portion 24 of the inserter 20. Once the threaded rod 22 has engaged the acetabular prosthesis 72, such as by a threaded engagement between the threads 28 of the threaded end 26 of the threaded rod 22 and the threaded hole 70 of acetabular prosthesis 72, the threaded rod 22 and the acetabular prosthesis 72 can be moved as an assembly generally in the direction of Arrow B into the handle extension 40 of the handle portion 24, as illustrated in FIG. 6.

The anti-rotation end 76 of the handle extension 40 can be moved into engagement over the anti-rotation portion 78 of the acetabular prosthesis 72, when the rod 22 and prosthesis 72 assembly is inserted into the handle extension 40. Accordingly, the acetabular prosthesis 72 can be engaged onto the threaded rod 22 either after insertion of the threaded rod 22 into the handle assembly 24 or prior to engagement of the handle portion 24 onto the threaded rod 22. The assembly of the acetabular prosthesis 72 onto the sleeve portion 40 of the handle body 24, however, can be provided to engage the acetabular prosthesis 72 into a substantially rotationally fixed configuration relative to the handle body 24. The rotational fixation provides for rotational selection and fixation of the acetabular prosthesis 72 relative to the handle body 24 for implantation into the acetabulum by a user.

According to various embodiments, including those described herein, the inserter 20 can engage the acetabular prosthesis 72 in both a rotationally fixed manner, such as rotation relative to the handle assembly 24, and in a positionally, e.g. axially, fixed manner, for implanting the acetabular prosthesis 72 into the pelvis 82 of a patient. The inserter 20 can be provided for substantially quick and efficient engagement of the acetabular prosthesis 72 in both a positionally and rotationally fixed manner relative to the handle body 24. The threaded rod 22 can be engaged into the acetabular prosthesis 72 separately from the handle body 24 by a user in an efficient manner. The rod 22 may alternatively engage the prosthesis 72 in combination by using the handle body 24 to engage the acetabular prosthesis 72. Alternatively, or in combination therewith, it is understood that a user can engage the second end 30 of the threaded rod 22 with a tool to rotate the threaded rod 22 into the acetabular prosthesis 72 with the use of a threading tool or handle 90.

Additionally, with reference to FIG. 7, the acetabular prosthesis 72 can be efficiently disengaged from the insertion assembly 20. In disengaging the insertion instrument 20 from the implanted acetabular prosthesis 72, the locking mechanism 42 can be moved in reverse of that described above. For example, with reference to FIG. 7, once the acetabular prosthesis 72 is selectively seated within the prepared acetabulum 80 of the pelvis 82, the locking sleeve 52 can be generally moved in the direction of Arrow B to allow disengagement of the locking ball bearings 50 from the second detent with the sleeve 52 moved in the direction of Arrow A the locking ball bearings 50 may also not engage the first detent 32. Once the bearings 50 are disengaged, the entire handle assembly 24 can be moved generally in the direction of Arrow A to remove the handle assembly 24, including the handle extension 40, from the threaded rod 22. Once the handle assembly 24 has been removed, generally in the direction of Arrow B, as illustrated in FIG. 8, the threaded rod 22 can be unthreaded from the acetabular prosthesis 72. For example, a threading tool or handle 90 can be used to unthread the threaded rod 22 from the acetabular prosthesis 72. Once unthreaded, the threaded rod 22 can be disengaged from the threaded hole 70 of the acetabular prosthesis 72. Once the threaded rod 22 is disengaged and removed from the acetabular prosthesis 72, a procedure can be completed, such as positioning a selected bearing within the acetabular prosthesis 72.

In this manner, the acetabular prosthesis 72 can be implanted into the acetabulum 80 of the pelvis 82 by first fixing the acetabular prosthesis 72 both positionally and rotationally relative to the implantation assembly 20. In addition, the acetabular prosthesis 72 can be removed or moved relative to the prepared acetabulum 80 by re-engaging the threaded rod 22 with the acetabular prosthesis 72 and repositioning the handle assembly 24 onto the threaded rod 22 in a manner as described above. Thus, a position of the prosthesis 72 can be altered prior to substantially permanent fixation, such as with setting of cement or positioning a screw through the prosthesis 72.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A system to position an acetabular cup prosthesis in a subject, comprising:
   a rod extending from a first threaded end of the rod to a second end of the rod;
   a handle member distinct from the rod and extending from a first end of the handle member to a second end of the handle member and defining an internal bore configured to receive at least a portion of the rod, wherein an outer wall of handle member at the first end of the handle member defines a keyed configuration;
   a connection mechanism to interconnect the rod within the bore of the handle member, the connection mechanism including a locking sleeve and a bearing member configured to be urged into contact with the rod by the locking sleeve for locking the rod axially within the bore of the handle member; and
   an acetabular cup prosthesis threaded onto the first threaded end of the rod to axially fix the acetabular cup prosthesis relative to the rod, wherein the acetabular cup prosthesis includes a keyed depression that is configured to receive the keyed configuration at the first end of the handle member for rotationally fixing the acetabular cup prosthesis relative to the handle member when the keyed configuration is received in the keyed depression,
   wherein the rod is configured to be moved within the bore of the handle member to move the first threaded end of the rod from a first pre-selected axial position relative to the handle member to at least a second pre-selected axial position relative to the handle member, wherein the rod is movable back and forth between the first pre-selected axial position and the second pre-selected axial position, wherein the first pre-selected axial position is at a different axial position relative to the handle member than the second pre-selected axial position, and wherein the rod is lockable within the bore of the handle member when the first threaded end of the rod is at the first pre-selected axial position and when the first threaded end of the rod is at the second pre-selected axial position,
   wherein, when the first threaded end of the rod is in the second pre-selected axial position relative to the handle member, the keyed configuration at the first end of the handle member is received in the keyed depression of the acetabular cup prosthesis to rotationally fix the acetabular cup prosthesis relative to the handle member.

2. The system of claim 1, wherein the rod has an outer surface that defines a first detent and a second detent which correspond to said first pre-selected axial position and said second pre-selected axial position, respectively, the first detent and the second detent each being located between the first threaded end of the rod and the second end of the rod with the second detent being longitudinally spaced apart a fixed distance from the first detent along the outer surface of the rod;
   wherein the bearing member is configured to separately engage both the first detent and the second detent.

3. The system of claim 2, further comprising:
   a biasing member configured to bias the locking sleeve in a first direction;

wherein the locking sleeve defines a ramp surface;
wherein when the bearing member is engaging at least one of the first detent or the second detent and the locking sleeve is biased in the first direction the rod is axially fixed relative to the handle member.

4. The system of claim 3, wherein, when the first threaded end of the rod is in the second pre-selected axial position, the bearing member is engaged in the second detent.

5. The system of claim 4, wherein the keyed configuration includes a non-circular outer surface.

6. The system of claim 1, wherein the rod further includes a first demarcation and a second demarcation;
wherein the handle member defines a mark window through the outer wall;
wherein the first demarcation is viewable through the mark window when the first threaded end of the rod is in the first pre-selected axial position and the second demarcation is viewable through the mark window when the first threaded end of the rod is in the second pre-selected axial position.

7. The system of claim 1, wherein the rod has an outer surface that defines at least a first detent that is discontinuous about the rod, wherein the bearing member is configured to engage the first detent to rotationally fix the rod relative to the handle member.

8. A system to position a prosthesis in a subject, comprising:
an elongated member having an exterior surface extending from a first threaded end of the elongated member to a second end of the elongated member, wherein the exterior surface defines a first detent and a second detent which are each located between the first threaded end of the elongated member and the second end of the elongated member, the first detent being longitudinally spaced apart a fixed distance from the second detent along the exterior surface of the elongated member;
a handle member having an outer wall extending from a first end of the handle member to a second end of the handle member and defining an internal bore configured to receive the elongated member through the first end of the handle member, wherein the outer wall of handle member at the first end of the handle member defines a keyed configuration;
a prosthesis threaded onto the first threaded end of the elongated member to axially fix the prosthesis relative to the elongated member, wherein the prosthesis includes a keyed depression that is configured to receive the keyed configuration at the first end of the handle member for rotationally fixing the prosthesis relative to the handle member when the keyed configuration is received in the keyed depression; and
a connection mechanism to interconnect the elongated member within the bore of the handle member, the connection mechanism including:
a locking sleeve,
a biasing member to bias the locking sleeve in at least a first direction, and
a fixing member configured to be urged into selected contact with the first detent of the elongated member with the locking sleeve for locking the elongated member axially within the bore of the handle member or with the second detent of the elongated member with the locking sleeve for locking the elongated member axially within the bore of the handle member;
wherein the elongated member is configured to be moved within the bore of the handle member to move the first threaded end of the elongated member from a first pre-selected axial position to at least a second pre-selected axial position relative to the handle member, wherein the elongated member is movable back and forth between the first pre-selected axial position and the second pre-selected axial position, the first pre-selected axial position corresponding to the first detent of the elongated member and the second pre-selected axial position corresponding to the second detent of the elongated member such that the first pre-selected axial position and the second pre-selected axial position are longitudinally spaced apart by said fixed distance, wherein, when the first threaded end of the elongated member is in the second pre-selected axial position relative to the handle member, the fixing member is contacting the second detent and the keyed configuration at the first end of the handle member is received in the keyed depression of the prosthesis to rotationally fix the prosthesis relative to the handle member.

9. The system of claim 8, further comprising:
a graspable portion extending from the second end of the handle member;
wherein the locking sleeve is operable to be moved along the handle member relative to the graspable portion.

10. The system of claim 8, wherein the elongated member further includes a first demarcation and a second demarcation;
wherein the handle member further includes a mark window through the outer wall;
wherein the first demarcation is viewable through the mark window when the first threaded end of the elongated member is in the first pre-selected axial position and the second demarcation is viewable through the mark window when the first threaded end of the elongated member is in the second pre-selected axial position.

11. The system of claim 8, wherein at least one of the first detent or the second detent includes a groove extending around the exterior surface of the elongated member.

12. The system of claim 8, wherein the first threaded end of the elongated member is configured to be threadably engaged to the prosthesis prior to positioning the first threaded end of the elongated member in either the first pre-selected axial position or the second pre-selected axial position relative to the handle member.

13. The system of claim 12, wherein the keyed configuration includes a non-circular outer surface.

14. The system of claim 13, wherein the prosthesis is an acetabular cup prosthesis.

* * * * *